United States Patent
Marais

(10) Patent No.: US 7,014,465 B1
(45) Date of Patent: Mar. 21, 2006

(54) IRRIGATING MEDIUM FOR ROOT CANALS AND METHOD

(75) Inventor: Jacobus Theodorus Marais, Pretoria (ZA)

(73) Assignee: Radical Waters IP (PTY) Ltd., Erasmuskloof (ZA)

(*) Notice: Subject to any disclaimer, the term of this patent is extended or adjusted under 35 U.S.C. 154(b) by 0 days.

(21) Appl. No.: 09/582,700

(22) PCT Filed: Dec. 24, 1998

(86) PCT No.: PCT/US98/27380

§ 371 (c)(1),
(2), (4) Date: Aug. 21, 2000

(87) PCT Pub. No.: WO99/34652

PCT Pub. Date: Jul. 8, 1999

(30) Foreign Application Priority Data

Dec. 30, 1997 (ZA) .................................. 97/11702

(51) Int. Cl.
*A61C 5/02* (2006.01)
(52) U.S. Cl. ..................................... 433/224
(58) Field of Classification Search ............... 433/224, 433/226; 424/49; 204/164
See application file for complete search history.

(56) References Cited

U.S. PATENT DOCUMENTS

| | | | | | |
|---|---|---|---|---|---|
| 3,996,126 | A | * | 12/1976 | Rasmussen | 204/271 |
| 5,731,008 | A | * | 3/1998 | Morrow | 424/613 |
| 5,932,171 | A | * | 8/1999 | Malchesky | 422/29 |
| 6,159,448 | A | * | 12/2000 | Winston et al. | 424/52 |
| 6,231,878 | B1 | * | 5/2001 | Komatu et al. | 424/405 |

OTHER PUBLICATIONS

Hayashi et al., "Successful Treatment of Mediastinitis after Cardiovascular Surgery Using Electrolyzed Acid Aqueous Solution," Artificial Organs, 1997, vol. 21, No. 1, pp. 39-42.*

* cited by examiner

*Primary Examiner*—Melba N. Bumgarner
(74) *Attorney, Agent, or Firm*—Nath & Associates PLLC; Gary M. Nath; Tanya E. Harkins

(57) ABSTRACT

This invention is the use of an aqueous solution in the preparation of an irrigating medium for use in the treatment of root canals. The aqueous solution is an electro-mechanically activated solution prepared by electrolysis of an aqueous solution of a salt and including an aqueous anion-containing and an aqueous cation-containing solution. The invention also extends to a method for irrigating root canals with the electro-mechanically activated solution, and an irrigating medium comprising the electro-chemically activated solution.

7 Claims, No Drawings they may be used as antiseptics in root canal treatment so as to reduce the proliferation of bacteria and other micro-organisms remaining in the root canal after obturation.

IRRIGATING MEDIUM FOR ROOT CANALS AND METHOD

INTRODUCTION AND BACKGROUND TO THE INVENTION

This invention relates to the use of antiseptics in root canal treatment so as to reduce the proliferation of bacteria and other micro-organisms remaining in the root canal after obturation.

Sodium hypochlorite is universally used as an antiseptic for root canal irrigation, its principal functions in root canal treatment being microbicidai, dissolving organic material and lubrication. However, a disadvantage of sodium hypochlorite is that it is highly toxic to human tissues and cells in concentrated form and potentially even fatal at the concentrations at which it is at its most effective as an irrigating medium.

OBJECT OF THE INVENTION

It is accordingly an object of this invention to provide a novel, relatively inexpensive and safe irrigating medium for root canals.

SUMMARY OF THE INVENTION

According to a first aspect of the invention there is provided the use of an aqueous solution in the preparation of an irrigating medium for use in the treatment of root canals, the aqueous solution being characterised in that it is electro-chemically activated. The electro-chemically activated aqueous solution may consist of an aqueous anion-containing and/or an aqueous cation-containing solution. The aqueous anion-containing solution and/or aqueous cation-containing solution may be prepared by means of electrolysis of an aqueous solution of a salt. The salt may be sodium chloride. In particular, it may be non-iodated sodium chloride or potassium chloride.

The anion-containing and the associated cation-containing solution may be produced by an electrochemical reactor or so-called electrolysis machine. The anion-containing solution is referred to hereinafter for brevity as the "anolyte solution" and the cation-containing solution is referred to hereinafter for brevity as the "catholyte solution". The anolyte solution and the catholyte solution are preferably provided from an electrochemical reactor comprising a through-flow, electro-chemical cell having two co-axial electrodes with a co-axial diaphragm between them so as to separate an annular inter-electrode space into cathodic and anodic chambers.

The anolyte solution may be produced from a 10% aqueous NaCl solution, electrolysed in the anodic chamber to produce activated or excited aqueous solutions containing numerous free radicals, the anolyte solution having an extremely high redox potential of up to about +1170 mV and a pH value of about 2–7. These activated radical species may be labile and after about 96 hours the various radical species may disappear with no residues being produced.

The anolyte solution may include activated radical species such as ClO; ClO$^-$; HClO; OH$^-$; HO$_2^-$; H$_2$O$_2$; O$_3$; HO; S$_2$O$_8^{2-}$ and Cl$_2$O$_6^{2-}$.

The activated radical species have been found to have a synergistic anti-bacterial and/or anti-viral effect which is generally stronger than that of chemical bactericides and has been found to be particularly effective against viral organisms, spore and cyst forming bacteria including Gram positive and Gram negative bacteria such as *Enterococcus faecalis* and *Pseudomonas aeruginosa*.

The catholyte solution generally may have a pH of up to about 7–13 and a redox potential of about −980 mV. The catholyte solution may include activated radical species such as NaOH; KOH; Ca(OH)$_2$; Mg (OH)$_2$; HO; H$_3$O$_2^-$; HO$_2^-$; H$_2$O$_2^-$; O$_2^-$; OH$^-$; O$_2^{2-}$.

It is believed that the activated oxidising radical species or free radicals present in the anolyte solution act synergistically as a biocidal and virucidal agent at a bacterial cellular level, while the activated reducing radical species or free radicals present in the catholyte solution act synergistically as a cleaning agent to dissolve organic material or biofilm protecting or covering micro-organisms and with the micro-organisms themselves.

It has been found that the efficacy of the use of the anolyte and/or catholyte solution in the preparation of an irrigating medium for use in the treatment of root canals depends upon the concentration of the anolyte and/or the catholyte solutions, as measured by the oxidation-reduction potential (ORP) or redox potential of the anolyte and/or the catholyte solution, the exposure time, i.e. the contact time between the root canal and the anolyte and/or the catholyte solutions and the temperature during application. Anolyte has been found to be more effective at lower than at higher temperatures.

According to a second aspect of the invention there is provided an irrigating medium for irrigating root canals, the irrigating medium comprising an aqueous solution being substantially as hereinbefore defined.

According to a third aspect of the invention there is provided a method for irrigating root canals including the step of applying an electro-chemically activated aqueous solution to a root canal, substantially as hereinbefore defined.

DETAILED DESCRIPTION OF THE INVENTION

The method of irrigating root canals may include the steps of first applying catholyte solution to the root canal, aimed at removing organic biofilm and debris covering the inner walls of the root canal, and thereafter applying anolyte solution to the root canal, aimed at disinfecting the inner walls of the root canal and inner tubes in a tooth.

A preferred embodiment of the invention will now be described by means of two non-limiting examples.

1. EXAMPLE NO. 1

20 single rooted teeth were collected from the Department of Oral and Maxillofacial Surgery of the Faculty of Dentistry of the University of Pretoria, South Africa, immediately after extraction from patients' mouths.

1.1 Testwork

The extracted teeth were rinsed under running potable water and stored in specimen bottles filled with distilled water for 24 hours. The pulp chambers of the teeth were then accessed by the use of fissure burs in turbine handpieces and round burs in contra-angle handpieces.

A number 15 K-type root canal file was then introduced into each root canal to establish the patency of the canal. The exact length of each canal was determined by inserting a file into the root canal until its tip just appeared through the apical foramen. A silicone rubber stop pre-fitted to the shaft of the file was then adjusted to a coronal reference point, an intact part of the tooth.

The file was then withdrawn and the length from file tip to silicone stop was noted. An individual working length for each tooth was calculated by subtracting 1 mm from the measured length. The coronal thirds of all canals were pre-flared using Gates Glidden burs in a contra-angle handpiece. At this stage, the 20 teeth were randomly divided into two groups, namely Group A and Group B, for irrigation with the conventional sodium hypochlorite and the electro-chemically activated solution (STEDS) in accordance with the present invention respectively, each group consisting of 10 teeth.

Group A (Sodium Hypochlorite):

The root canals of Group A were prepared, using a series of K-type files (size 15–60) manually and by irrigating with a 2.5% solution of sodium hypochlorite, with an ultrasonic unit such as a so-called Cavi-Endo (Dentsply) unit. Irrigation was performed after the use of every size file for at least 10 seconds, using the same ultrasonic unit.

After the canal was prepared to a size 60, a final flush of irrigation was carried out for a minimum of 30 seconds. A minimum of 150 ml of 2.5% sodium hypochlorite was used in the irrigating process of each tooth.

Group B (Electro-Chemically Activated Solution "STEDS")

STEDS was produced from a specially manufactured electro-chemical reactor, comprising a through flow, electrochemical cell having two co-axial cylindrical electrodes with a co-axial diaphragm between them so as to separate an annular inter-electrode space into cathodic and anodic chambers. The STEDS produced included two separate solutions, namely catholyte and anolyte solutions. The anolyte solution had a pH of about 7.4 and a redox potential of about +1170 mV. The catholyte solution had a pH of about 9.5 and a redox potential of about −980 mV. These solutions were used to irrigate the canals in Group B. Root canals were prepared using the same size and types of files and the same manual techniques as in Group A. Initially the catholyte solution was used to irrigate the canals using the same ultrasonic unit as group B. After the use of each size file, the canal was irrigated with anolyte solution for at least 10 seconds.

After preparation to a size 60, a final flush of irrigation was carried out for a maximum of 30 seconds using catholyte solution. A minimum of 100 ml anolyte and 50 ml catholyte solutions were used for each tooth.

Immediately after the above preparation and irrigation procedures had been carried out, the teeth were again stored in distilled water for 24 hours. Each tooth was then dissected with the aid of a microtome. Specimens of the root canal walls of the middle third of the roots, measuring roughly 2 mm by 2 mm, were prepared. The specimens were handled with locking forceps throughout, eliminating contamination by human hand. The specimens were placed into a dust-free incubator and allowed to air-dry for 10 days.

The air-dried specimens were mounted with conductive adhesive onto metal bases and coated with gold and viewed in a scanning electron microscope at various magnifications. The amount of remaining debris on the root canal walls were compared by noting the debris on the surfaces of twenty representative samples of each group.

1.2 Results

The remaining debris in Group B was negligible. Group A exhibited small but noticeable amounts of debris on the surface of a number of specimens. In group B, it was noticed that the so-called smear layer, clearly present in all samples of Group A, had been removed in large areas.

Under the conditions of this study, STEDS compared favourably as an irrigating material with sodium hypochlorite. It removed a large degree of debris from the surfaces of the prepared root canal walls.

2. EXAMPLE 2

2.1 Testwork 69 extracted teeth, had their root canals prepared in the same manner as in Example 1. The teeth were then sterilized by means of an autoclave and were placed under aseptic conditions in 200 ml of BHl (brain-heart infusion) liquid culture medium together with 1.0 ml of an overnight broth culture of each of the following organisms: *E. faecalis, P. aeruginosa* and *S. mutans*. The teeth were kept in this broth for 7 days in an incubator at 37° C.

At the end of the 7 day period, the teeth were removed with a pair of sterile forceps from the broth. The bioload was expected to be extremely high by this time and colony counts were performed on the broth by doing a series of 10-fold dilutions in triplicate. Aliquots of these dilutions (100 $\mu$l) were spotted on 10% blood agar plates and spread with a sterile metal spreader over the surface of the plates. After overnight incubation at 37° C., these plates were counted and the number of colony-forming units (cfus) estimated.

The teeth were washed together in a sterile bottle with 100 ml of normal saline, repeated 4 times, with fresh saline being added after the contaminated saline was discarded. This reduced the bioburden to a level where the technologist carrying out the procedure was unlikely to develop an infection from spray aerosols.

The teeth were placed with the access cavity side facing upwards in sterile micro titre trays. Prior to treatment, all the teeth were "irrigated" down the access cavity with 50 ml sterile water using a syringe, for 5 minutes, this being similar to a manual irrigation procedure in the dental surgery. The teeth were then held upside-down for a few seconds to allow most of the water to drain off. The teeth were then divided into different groups for the various treatments.

Three groups of 20 teeth each were created, with three individual teeth serving as the catholyte control group and the six other teeth for whole tooth studies.

In Group A (negative control) all the teeth's root canals were irrigated with saline for 5 minutes, using a fine-needle tuberculin syringe. 30 $\mu$l saline was then aspirated from the root canals, serially diluted and spread plated onto 10% blood agar plates and incubated at 37° C. for 24 hours.

In Group B, 20 teeth were similarly treated with sodium hypoclorite for 5 and 10 minutes respectively. After 5 minutes and again after 10 minutes, the canals were filled with saline, and 30 $\mu$l saline were then aspirated, diluted, plated, and incubated.

In Group C all teeth were first treated with catholyte for 5 minutes. After this time, the catholyte was rinsed off with anolyte solution. The teeth were then treated with anolyte for 5 and 10 minutes respectively. At the end of these periods, the same culturing procedure, using saline, was used to take samples from the root canals.

Whole tooth studies were conducted on six of the teeth, as mentioned above. Two of the teeth were stored in sodium hypochlorite and cultures taken after 5 and 10 minutes. The two remaining teeth were stored in the catholyte, rinsed with and stored in the anolyte. Cultures were taken after 5 and 10 minutes storage time.

2.2 Results

2.2.1 Baseline Counts

The broth was shown to contain $4.4 \times 10^{10}$ cfus after 7 days' incubation with frequent additions of fresh culture medium. The average numbers of organisms present in the root canals after treatment with saline only was $1.4 \times 10^6$ cfus. The reason for this high count was that most of the organisms remained behind as a biofilm. An unexpected finding was that following catholyte treatment (with no anolyte), the count went up to $2 \times 10^7$ cfus. This is presumably because catholyte is known to act in a similar way to a detergent, lifting the biofilm from the surface.

2.2.2 Test Products

| AVERAGE NUMBER OF COLONY-FORMING UNITS IN ROOT CANALS OBTAINED AFTER EXPOSURE | | |
| --- | --- | --- |
|  | SODIUM HYPOCHLORITE | ANOLYTE |
| 5 minutes exposure | 0 | 400 |
| 10 minutes exposure | 0 | 0 |

2.2.3 Whole Tooth Counts

When the teeth were treated with sodium hypochlorite only for 5 minutes, the average count was $4 \times 10^2$ cfus. The counts dropped to zero when left for 10 minutes.

Using anolyte only (no catholyte pre-treatment) the average count was $1.2 \times 10^5$. However, when the teeth were exposed to catholyte, irrigated and then treated with anolyte for 10 minutes, the count dropped to zero.

This in vitro study shows that anolyte is highly effective in eradicating both planktonic and sessile organisms adherent to the tooth surface.

It is important that catholyte be applied first and then the catholyte and the loosened biofilm MUST be rinsed off for really effective results with the anolyte treatment.

It will be appreciated that many variations in detail are possible without departing from the scope and/or spirit of the invention as defined in the claims hereinafter.

What is claimed is:

1. A method for treating root canals, the method comprising the steps of: electrochemically activating an aqueous solution in an electro-chemical reactor comprising a through-flow, electro-chemical cell having two co-axial electrodes with a co-axial diaphragm between them so as to separate an annular inter-electrode space into cathodic and anodic chambers, wherein the electro-chemically activated solution produces an aqueous predominantly anion-containing solution and an aqueous predominantly cation-containing solution having microcidal, as well as dispersing and surfactant, properties; and applying the aqueous predominantly anion-containing solution and aqueous predominantly cation-containing solution either concurrently or successively to a root canal.

2. The method of claim 1, wherein the aqueous predominantly anion-containing solution and the aqueous predominantly cation-containing solution are prepared by means of electrolysis of an aqueous solution of a salt.

3. The method of claim 1 wherein the anion-containing solution is produced from a 10% aqueous NaCl solution, electrolysed to produce separable activated or excited radical cation and radical anion species, the anion-containing solution having a redox potential of up to about +1170 mV.

4. The method of claim 1 wherein the anion-containing solution has a pH of about 2 to 7 and a redox potential of about +1170 mV.

5. The method of claim 1 wherein the cation-containing solution has a pH of between 7 and 13 and a redox potential of about −980 mV.

6. A method of irrigating root canals, the method comprising the steps of electrochemically activating an aqueous solution in an electro-chemical reactor comprising a through-flow, electro-chemical cell having two co-axial electrodes with a co-axial diaphragm between them so as to separate an annular inter-electrode space into a cathodic and an anodic chamber, such that the electro-chemically activated aqueous solution includes an aqueous predominantly anion-containing and an aqueous predominantly cation-containing solutions having microcidal, as well as dispersing and surfactant properties; and applying the aqueous predominantly anion-containing and aqueous predominantly cation-containing solution either concurrently or successively to a root canal for irrigation purposes.

7. The method as claimed in claim 6 further including the steps of first applying cation-containing solution to the root canal, aimed at removing organic film and debris covering the inner walls of the root canal, and thereafter applying an anion-containing solution to the root canal, aimed at disinfecting the inner walls of the root canal and dentinal tubules.

* * * * *